(12) United States Patent
Messerschmidt et al.

(10) Patent No.: US 8,988,372 B2
(45) Date of Patent: Mar. 24, 2015

(54) OBTAINING PHYSIOLOGICAL MEASUREMENTS USING A PORTABLE DEVICE

(75) Inventors: Robert G. Messerschmidt, Los Altos, CA (US); Christopher D. Brown, Los Gatos, CA (US)

(73) Assignee: Avolonte Health LLC, Wilmington, DE (US)

(*) Notice: Subject to any disclaimer, the term of this patent is extended or adjusted under 35 U.S.C. 154(b) by 102 days.

(21) Appl. No.: 13/402,452

(22) Filed: Feb. 22, 2012

(65) Prior Publication Data

US 2013/0215042 A1 Aug. 22, 2013

(51) Int. Cl.
| G09G 3/36 | (2006.01) |
| G06F 3/041 | (2006.01) |
| G06F 19/00 | (2011.01) |

(52) U.S. Cl.
CPC ............ *G06F 3/041* (2013.01); *G06F 19/3406* (2013.01); *G09G 3/36* (2013.01)
USPC ............................................. 345/173; 345/87

(58) Field of Classification Search
CPC ..................................................... G06F 19/34
USPC .......... 600/300, 301, 509, 443, 512; 345/650, 345/173; 455/66.1, 575.8
See application file for complete search history.

(56) References Cited

U.S. PATENT DOCUMENTS

| 2007/0177298 | A1* | 8/2007 | Jaatinen et al. ................ 360/123 |
| 2009/0203998 | A1* | 8/2009 | Klinghult et al. ............. 600/443 |
| 2010/0179446 | A1* | 7/2010 | Bojovic et al. ................ 600/512 |
| 2011/0034786 | A1  | 2/2011 | Cadio et al. |
| 2011/0306859 | A1  | 12/2011 | Saldivar et al. |
| 2012/0016210 | A1  | 1/2012 | Kim et al. |
| 2012/0022385 | A1* | 1/2012 | Shimuta et al. ............... 600/509 |
| 2012/0172684 | A1* | 7/2012 | Buchheim et al. ............ 600/301 |
| 2012/0249438 | A1* | 10/2012 | Kim et al. ...................... 345/173 |
| 2013/0120459 | A1* | 5/2013 | Dickinson et al. ............ 345/650 |

FOREIGN PATENT DOCUMENTS

| TW | 201338752 A | 10/2013 |
| WO | WO-2013126530 A2 | 8/2013 |
| WO | WO-2013126530 A3 | 8/2013 |

OTHER PUBLICATIONS

"International Application Serial No. PCT/US2013/027073, International Preliminary Report on Patentability mailed Sep. 4, 2014", 9 pgs.

Bedogni, G., et al., "Accuracy of an eight-point tactile-electrode impedance method in the assessment of total body water.", *Eur J Clin Nutr.*, 56(11), (Nov. 2002), 1143-1148.

(Continued)

*Primary Examiner* — Seokyun Moon
*Assistant Examiner* — Peijie Shen
(74) *Attorney, Agent, or Firm* — Schwegman Lundberg & Woessner, P.A.

(57) ABSTRACT

An apparatus and method for obtaining a physiological measurement associated with a user using a portable device is disclosed herein. Information displayed on a touch-sensitive display of the portable device specifies the contact area(s) on the portable device for a user to touch. One or more areas on the portable device and/or a detachable device connected to the portable device comprise conductive areas for measuring the resistance or impedance of the user's body between those conductive areas.

24 Claims, 12 Drawing Sheets

(56) References Cited

OTHER PUBLICATIONS

Kyle, U. G, et al., "Bioelectrical impedance analysis—part 1: review of principles and methods", *Clin Nutr.*, 23(5), (Oct. 2004), 1226-1243.

"International Application Serial No. PCT/US2013/027073, International Search Report mailed Nov. 4, 2013", 4 pgs.

"International Application Serial No. PCT/US2013/027073, Written Opinion mailed Nov. 4, 2013", 7 pgs.

"Sensors", XP002714777, [Online]. Retrieved from Internet: <http://web.archive.org/web/20111202210338/http://www.gsmarena.com/glossary.php3.>, (Dec. 2, 2011).

\* cited by examiner

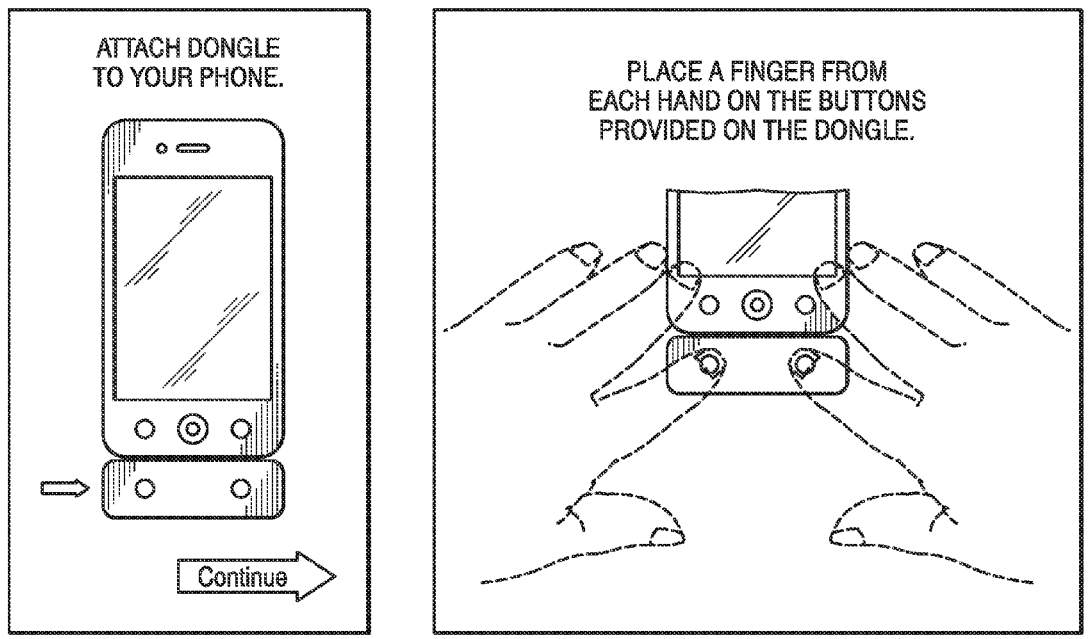

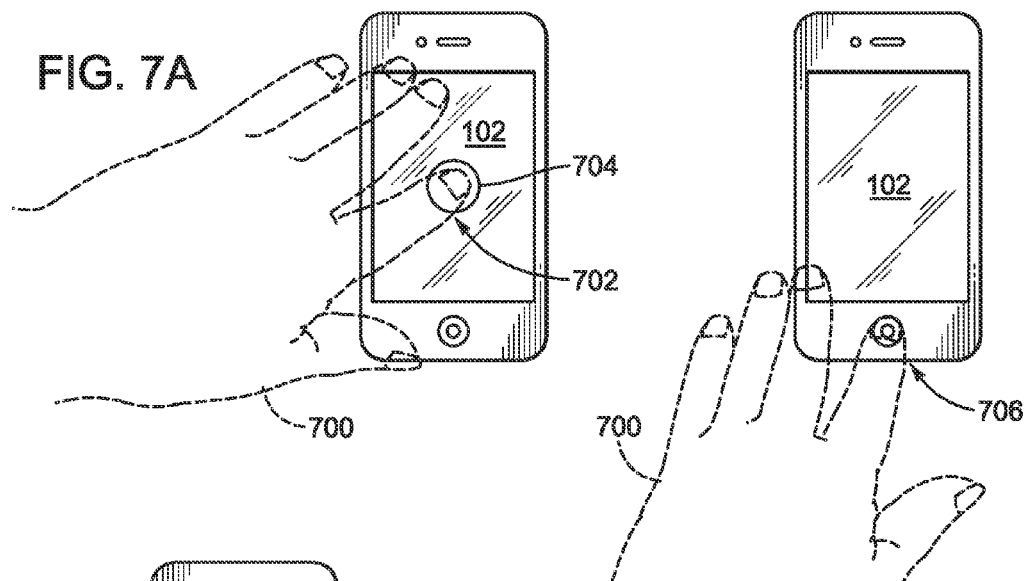
FIG. 7A
FIG. 7B
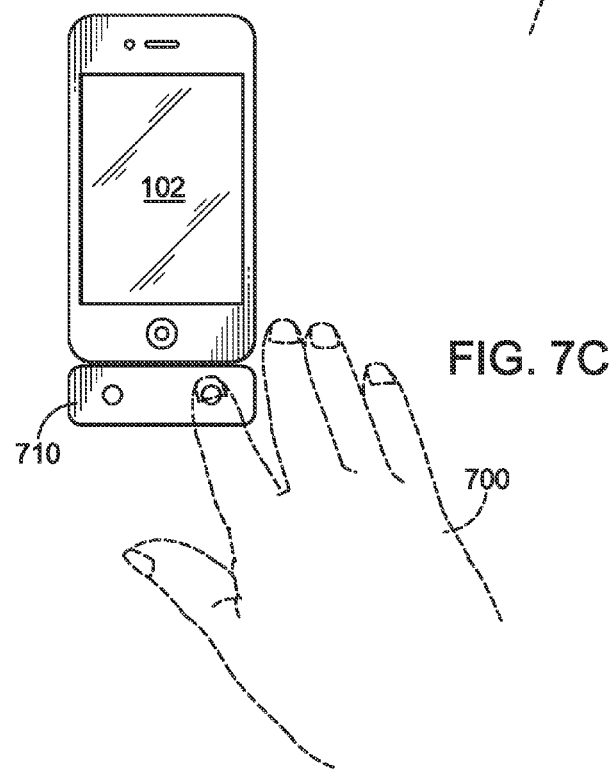
FIG. 7C

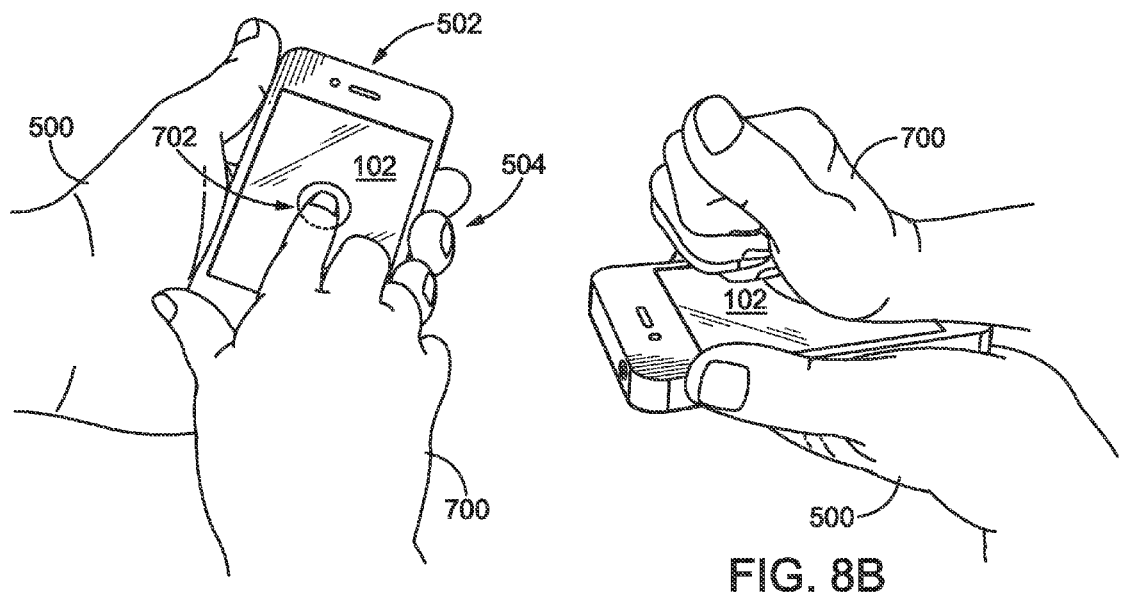
FIG. 8A
FIG. 8B
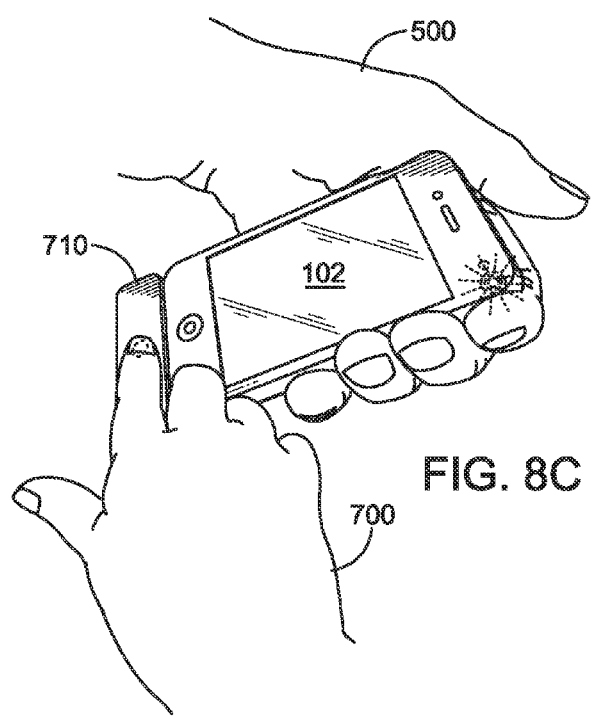
FIG. 8C

OBTAINING PHYSIOLOGICAL MEASUREMENTS USING A PORTABLE DEVICE

TECHNICAL FIELD

The present disclosure relates to obtaining physiological measurement in general, and in particular embodiments, to obtaining physiological measurements using a portable device.

BACKGROUND

In recent years there has been an increase in health awareness as people live longer, more people become overweight, and the cost of health care rises. One of the ways to take better care of yourself is by basic monitoring of your physiological state. Physiological measurements, such as pulse, electrocardiogram (ECG), body fat, or body hydration measurements, are common in sports and wellness fields. Examples of current measurement devices include wrist watches that measure pulse rates, a chest strap with a loop and hook closure, calipers to measure body fat, water scales to measure body fat, and a set of electrodes attached to various parts of a torso for ECG measurements. Conventional physiological measurement devices tend to be dedicated devices in that they are designed to serve a single purpose for use in obtaining a particular type of physiological measurement. Body fat calipers, for example, cannot also be used to obtain ECG measurements or be used for other purposes.

A limitation of current physiological measurement devices is relative high cost and complexity of use. The relative high cost arises due to a small customer base of sports and wellness users as opposed to the general population. Sports and wellness enthusiasts are also more willing to pay more for a perceived specialty device than the public at large. The small customer base also means less design resources are likely to be devoted to the product. The end result is a device that requires pre-existing knowledge by the user and requires consulting (repeatedly) a user's manual in order to properly use the device.

BRIEF SUMMARY

In certain embodiments, portable devices, such as smart phones and tablets, are used to generate one or more physiological measurements associated with a user. In some embodiments, the user interacts with the portable device as he/she normally would, and the portable device is configured to sense physiological parameter(s) about the user and translate it into useful health assessment information. In other embodiments, the user may be instructed by the portable device to position portions of his/her body in a certain way relative to the portable device to provide the physiological parameter(s). Sensed physiological parameter(s) are converted into physiological measurements such as, but not limited to, ECG measurements, pulse measurements, body fat content measurements, and/or body water content measurements.

Other features and aspects of the invention will become apparent from the following detailed description, taken in conjunction with the accompanying drawings which illustrate, by way of example, the features in accordance with embodiments.

BRIEF DESCRIPTION OF THE DRAWINGS

Some embodiments are illustrated by way of example and not limitations in the figures of the accompanying drawings, in which:

FIGS. 4A-4F illustrate exemplary user interface presented on the touch sensor panel of the portable device to provide instructions on how to use the portable device to obtain physiological measurement(s).

FIGS. 7A-7C illustrate exemplary portions of the user's body that may contact the various embodiments of the second contact area according to some embodiments.

Figure 1A:
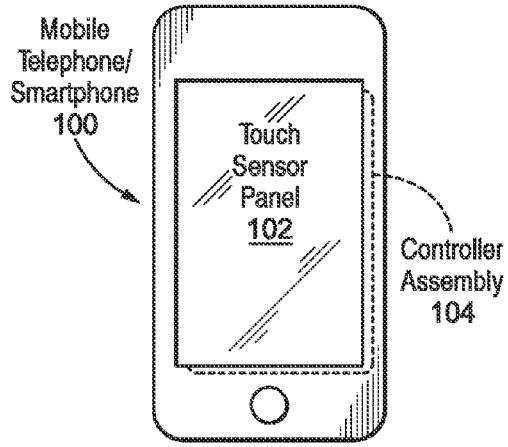
FIGS. 1A-1D illustrate exemplary portable devices used to obtain physiological measurements according to some embodiments.
Figure 1B:
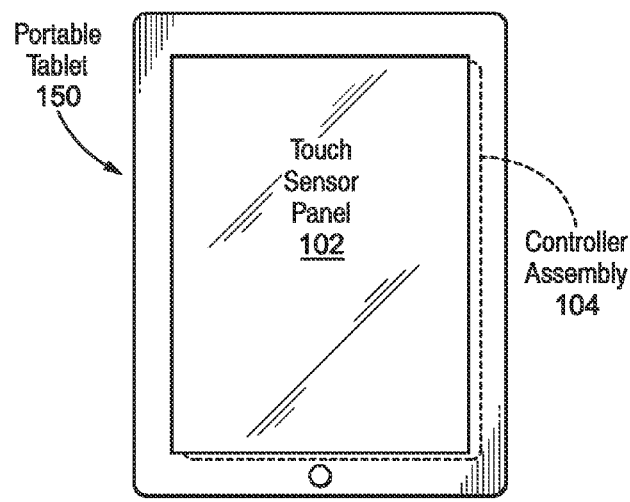
Figure 1C:
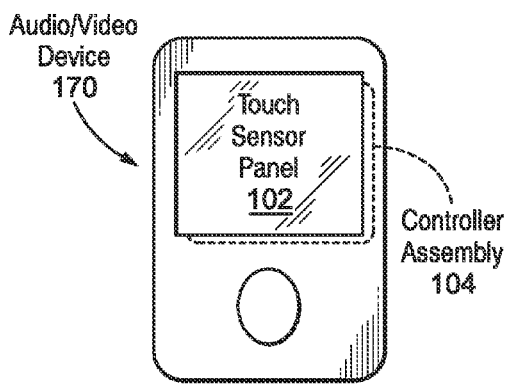
Figure 1D:
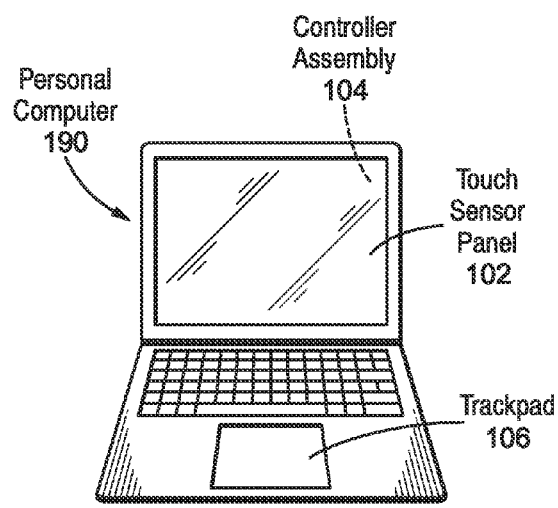

The headings provided herein are for convenience only and do not necessarily affect the scope or meaning of the terms used.

DETAILED DESCRIPTION

The following detailed description refers to the accompanying drawings that depict various details of examples selected to show how the present invention may be practiced. The discussion addresses various examples of the inventive subject matter at least partially in reference to these drawings, and describes the depicted embodiments in sufficient detail to enable those skilled in the art to practice the invention. Many other embodiments may be utilized for practicing the inventive subject matter than the illustrative examples discussed herein, and many structural and operational changes in addition to the alternatives specifically discussed herein may be made without departing from the scope of the inventive subject matter.

In this description, references to "one embodiment" or "an embodiment," or to "one example" or "an example" mean that the feature being referred to is, or may be, included in at least one embodiment or example of the invention. Separate references to "an embodiment" or "one embodiment" or to "one example" or "an example" in this description are not intended to necessarily refer to the same embodiment or example; however, neither are such embodiments mutually exclusive, unless so stated or as will be readily apparent to those of ordinary skill in the art having the benefit of this disclosure. Thus, the present invention can include a variety of combinations and/or integrations of the embodiments and examples described herein, as well as further embodiments and examples as defined within the scope of all claims based on this disclosure, as well as all legal equivalents of such claims.

For the purposes of this specification, a "processor-based system" or "processing system" as used herein, includes a system using one or more microprocessors, microcontrollers and/or digital signal processors or other devices having the capability of running a "program," (all such devices being referred to herein as a "processor"). A "program" is any set of executable machine code instructions, and as used herein, includes user-level applications as well as system-directed applications or daemons.

FIGS. 1A-1D illustrate exemplary portable devices used to obtain physiological measurements according to some embodiments. A portable device comprises, but is not limited to, a mobile telephone or smart phone 100, a portable tablet 150, an audio/video device 170, a personal computer 190 such as a laptop or netbook, any variety of mobile devices that include a touch sensor panel, or the like. Each of the mobile telephone/smart phone 100, portable tablet 150, audio/video device 170, and personal computer 190 includes a touch sensor panel 102 (also referred to as a touch sensitive display, touch sensitive screen, or a touchpad) and a controller assembly 104. The touch sensor panel 102 includes an array of pixels to sense touch event(s) from a user's finger, other body parts, or objects. Examples of touch sensor panel 102 includes, but is not limited to, capacitive touch sensor panels, resistive touch sensor panels, infrared touch sensor panels, and the like. The controller assembly 104 is configured to provide processing capabilities (discussed in detail with reference to FIG. 10) for the portable device.

Each of the mobile telephone/smart phone 100, portable tablet 150, audio/video device 170, and personal computer 190 may also include a power button, a menu button, a home button, a volume button, a camera, a light flash source for the camera, and/or other components to operate or interface with the device.

Figure 2:
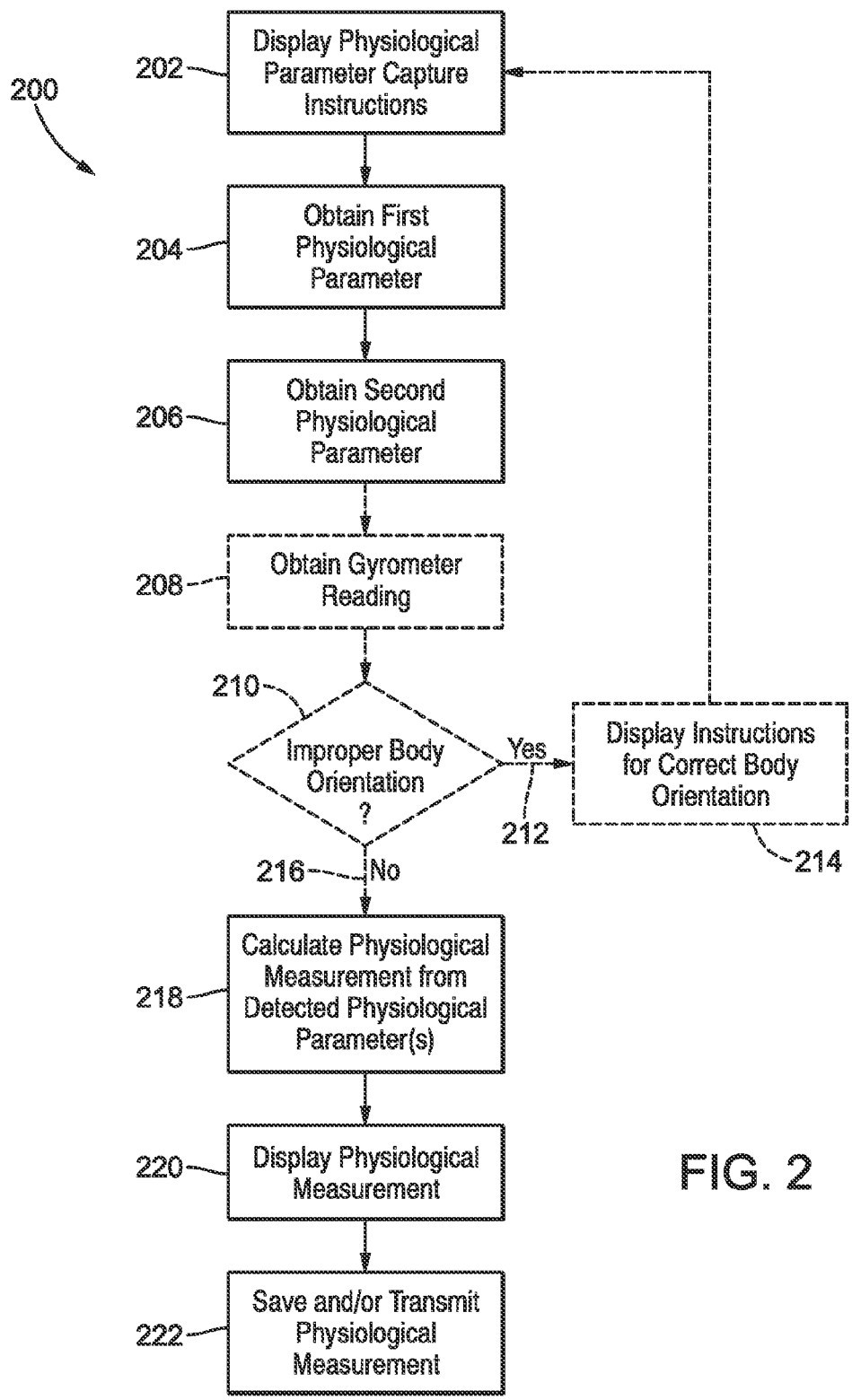
FIG. 2 illustrates an exemplary flow diagram for obtaining physiological measurements using a portable device in accordance with some embodiments.
Figure 3:
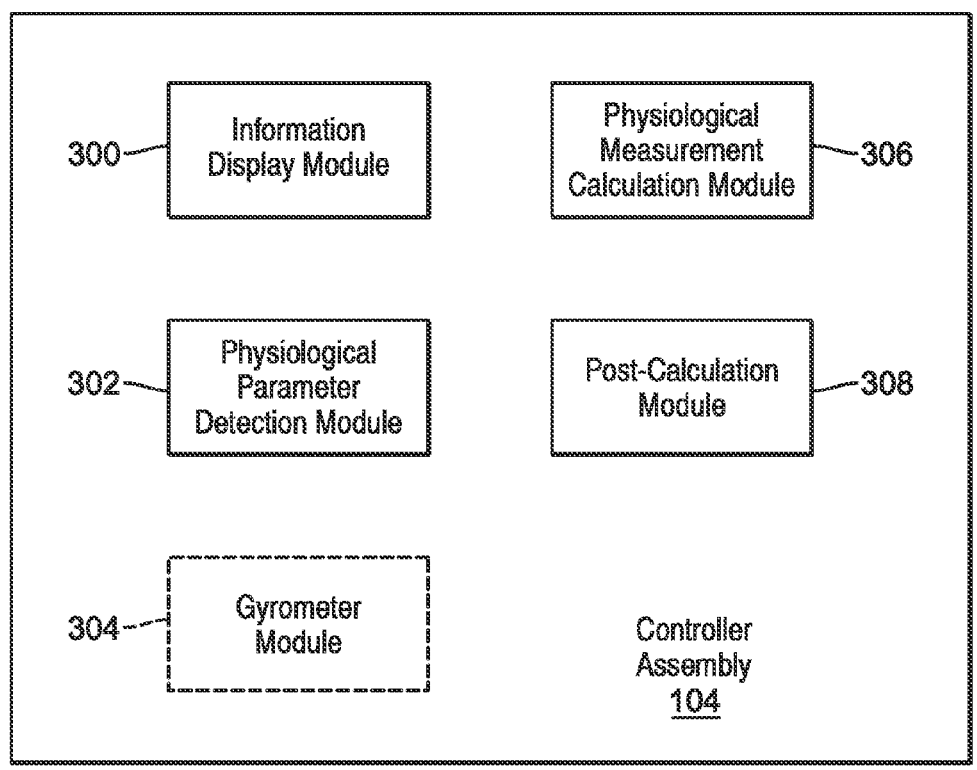
FIG. 3 illustrates a block diagram showing modules configured to facilitate the process of flow diagram of FIG. 2.

FIG. 2 illustrates an exemplary flow diagram 200 for obtaining physiological measurements using a portable device in accordance with some embodiments. FIG. 3 illustrates a block diagram showing modules configured to facilitate the process of flow diagram 200. The modules shown in FIG. 3 are included in the controller assembly 104. The modules of FIG. 3 comprise conceptual modules representing instructions encoded in a computer readable storage device. When the information encoded in the computer readable storage device are executed by the controller assembly 104, computer system or processor, it causes one or more processors, computers, or machines to perform certain tasks as described herein. Both the computer readable storage device and the processing hardware/firmware to execute the encoded instructions stored in the storage device are components of the portable device. Although the modules shown in FIG. 3 are shown as distinct modules, it should be understood that they may be implemented as fewer or more modules than illustrated. It should also be understood that any of the modules may communicate with one or more components external to the portable device via a wired or wireless connection.

FIG. 2 will be discussed in reference to FIG. 3, as well as to other figures herein, which further depict examples of operation of various embodiments of the devices described herein. In FIG. 2, at a block 202, the touch sensor panel 102 displays information to a user of the portable device to initiate capture of the user's physiological parameters. An information display module 300 is configured to generate and facilitate information for display on the touch sensor panel 102. Information presented to the user includes, but is not limited to, textual, graphical, animation, image, and/or video instructions on how and where to touch the portable device for the portable device to capture the desired physiological parameters. Such information may also be provided to the user in an audio format, either automatically or in response to the user's request. The user interface providing capture information/instruction to the user can comprise one or more interface pages or screens depending on, for example, the particular physiological measurement to be obtained, desired contact location(s) on the portable device, or the portable device's display size.

Physiological measurements aid in health assessment and health awareness. Physiological measurements may be medically recommended due to a health condition or a person may wish to know quantitative or qualitative information about his body for fitness, dietary, or other purposes. Examples of physiological measurements include, but are not limited to, electrocardiogram (ECG) measurements, pulse measurements (also referred to as heart rate or pulse rate measurements), body fat content measurements, blood pressure, and body water content measurements.

In one embodiment, physiological measurements are obtained by having a user simultaneously touch a portable device at two locations, thereby creating a closed electrical circuit including the user. The two contact locations on the portable device comprise electrodes (also referred to as conductors or sensors). This action permits the portable device to capture electrical characteristics of the user and translate the captured information into well-understood physiological measurements such as pulse rate. In the case of ECG or pulse measurements, the captured electrical characteristics comprise measuring the resistance between the two locations on the user's body that are in contact with the portable device. In the case of body fat or water content measurements (part of bioelectrical impedance analysis (BIA)), the captured electrical characteristics comprise measuring the impedance between the two locations on the user's body that are in contact with the portable device. The accuracy of the measurements increase when the two locations on the user's body that contact the device are from opposite sides of the user's torso (e.g., from each of the user's left and right extremities) at least for cardiac-related measurements.

In another embodiment, physiological measurements are obtained by having a user simultaneously touch a light source and a light sensor, located near the light source, on a portable device. A light from the light source enters the portion of the user's body that is in contact with the light source (e.g., finger tip), and a reflected light exits the portion of the user's body for detection by the light sensor. The changing blood volume in the user's body, corresponding to the user's heartbeat, results in the reflected light being a train of light pulses. A single location on the user's body (e.g., a single contact location) is sufficient to measure the pulse using optical measurement methods.

Figure 4A:
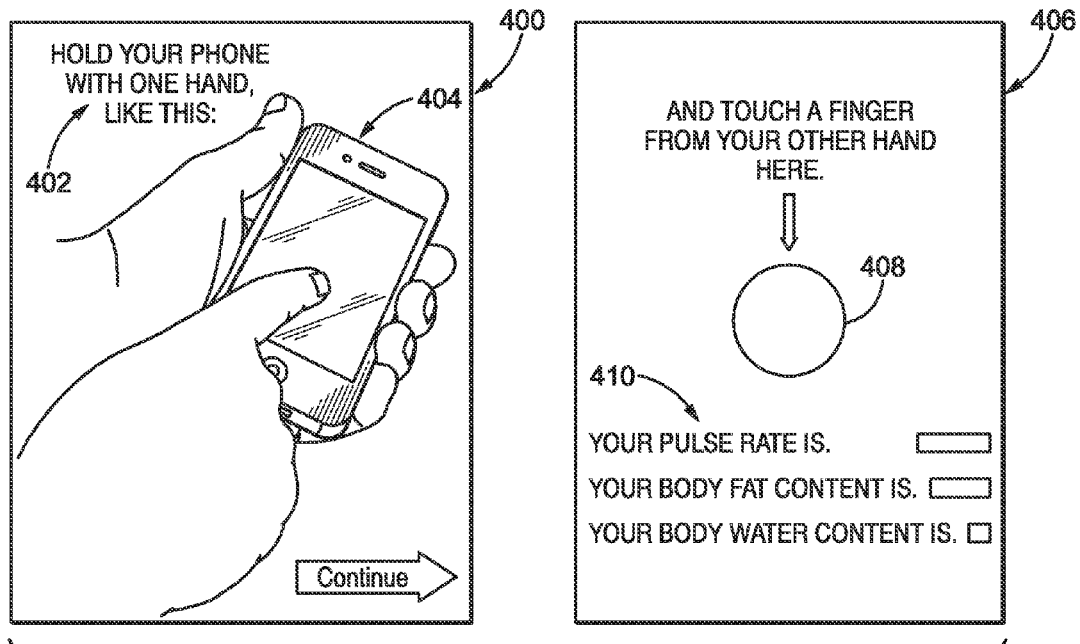
Figure 4B:
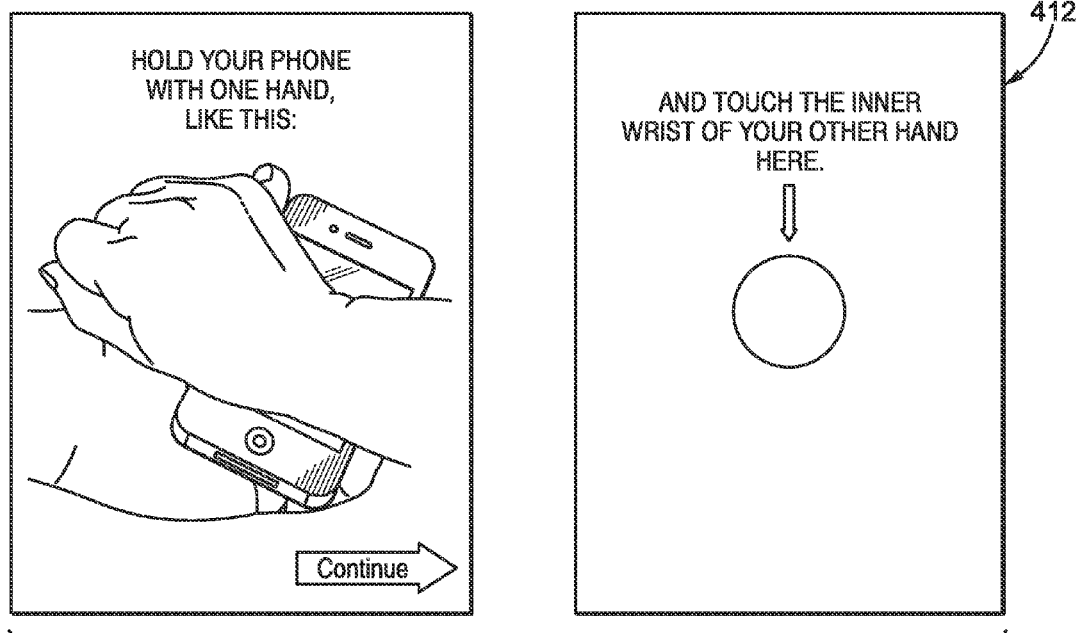

FIGS. 4A-4F illustrate exemplary user interface presented on the touch sensor panel 102 of the portable device to provide instructions (also referred to as guidance or directions) on how to use the portable device to obtain physiological measurement(s). In FIG. 4A, a first user interface page or screen 400 includes a textual item 402 and an image item 404, each providing instructions for making contact with a first electrode or sensor location on the portable device. The first user interface screen 400 instructs the user to hold or grip the portable device as he normally would when using the device (e.g., natural hold or gripping gesture). For example, if the back or side of the portable device comprises a conductive material (e.g., is metallic), naturally holding the device will provide sufficient contact with a first contact location. A second user interface page or screen 406 includes a graphical item 408 (also referred to as a contact location, area, or region identifier) (e.g., a circle) that specifies where on the touch sensor panel 102 the user's finger should touch to make sufficient contact with a second contact location. (To be discussed in detail below, the location of the graphical item 408 coincides with the location of a top conductive portion or layer of the touch sensor panel 102.) Once the user's physiological parameters from the first and second contact locations are captured by the portable device, the corresponding physiological measurements can be displayed in the second user interface page 406 as measurement items 410. In FIG. 4A, the pulse, body fat content, and body water content measurements can be displayed in the second user interface page 406. Notice that screens 400 and 402 provide detailed instructions such as where to touch the portable device, what part of the user's body should touch the portable device, and the like. FIG. 4B is similar to FIG. 4A except a second user interface page or screen 412 instructs the user to place his or her inner wrist to the designated second contact location. People are used to taking pulse measurements by counting their pulse on their inner wrist, and FIG. 4B shows a similar way for the user to obtain pulse measurements through use of the device.

Figure 4C:
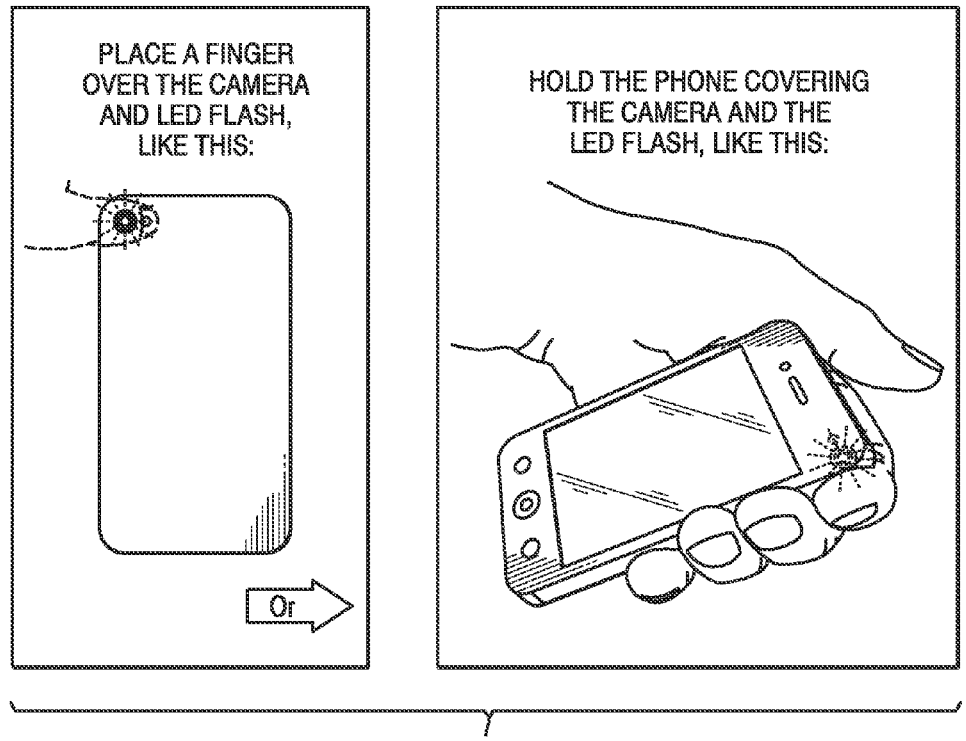
Figure 4D:
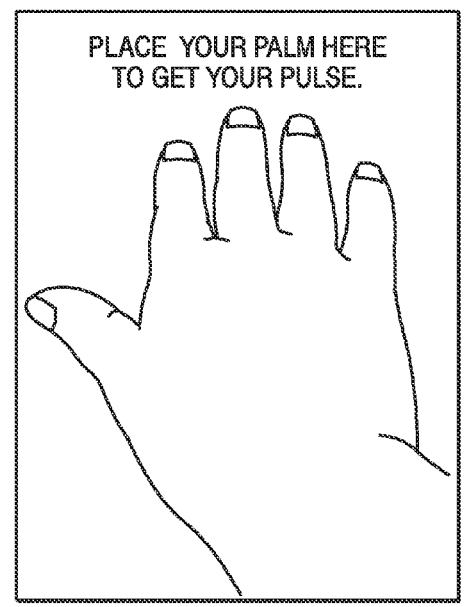

FIGS. 4C and 4D provide example instruction sets for optical capture of the user's physiological parameter. Note that depending on the size of the touch sensor panel 102, more than one user interface page may be combined into one user interface page. In FIG. 4D, if the touch sensor panel 102 of the portable device is about the size of or larger than a person's hand, such as may be the case when the portable device is the tablet 150, a graphical item 414 representative of a hand outline can be displayed to guide the user to place his/her palm on that area of the touch sensor panel 102.

FIGS. 4E and 4F provide example instruction sets to capture the user's physiological parameters using the portable device with a detachable (portable) device attached to the portable device. In FIG. 4E, a detachable dongle is connected to one or more data ports of the portable device. In the example of FIG. 4E, the detachable dongle includes a pair of buttons that serve as electrodes or sensor locations. The user places a finger from each of his/her right and left hands on the respective buttons to complete a circuit. The portable device processes the detected physiological data to present one or more physiological measurements (pulse, body fat content, body water content, etc.) on the touch sensor panel 102.

FIG. 4F illustrates instructions (in this example, only text information is provided although images, animation and other formats are also possible) in which the first contact location is located on a sleeve, case or cover of the portable device and the second contact location is located on the portable device. The sleeve or case should be attached to the portable device at the time of the data capture. At least a portion of the sleeve or case comprises conductive material (such as the portion of the sleeve coincident with the sides of the portable device). The second contact location may be any location on the touch sensor panel 102 (provided the panel 102 includes a top conductive layer throughout the panel). In some embodiments, one of the contact locations may be located at a remote location to the portable device; and may be in either wired or wireless communication with the portable device. For example, in some systems the contact location (for example, an optical sensor or source, or an electrical sensor or source) may be coupled via a wired connection to the portable device. In one example configuration, for example, an electrode (for either receiving or omitting a signal) might be placed in an earbud in a position to electrically contact the wearer when worn. The electrode can be coupled by a wire and connector contact to a suitably configured mating connector in the portable device.

It should be understood that FIGS. 4A-4F are merely provided as examples and other variations—in the way the portable device and/or additional attached device(s) captures the user physiological characteristics and/or in the manner in which instructions/guidance to the user may be presented—are within the scope of the invention. FIGS. 4A-4F should not be construed to be limiting as to what and how the portable device interacts with the user to facilitate capture of user physiological parameters.

Next at a block 204, a physiological parameter detection module 302 is configured to obtain a first physiological parameter associated with the user being in contact with a first contact area on the portable device (or detachable device as appropriate). The first contact area (also referred to as a first electrode, first sensor, first contact location, first contact region, etc.) may be located on the portable device or the detachable device that is appropriately attached to the portable device, as discussed in detail below. The material at the first contact area that comes into (electrical) contact with the user comprises a conductive material such as, but not limited to, a metallic material, or another material having a sufficiently low electrical resistivity to allow function as an electrode for purposes of the intended measurements.

For physiological measurements based on the circuit-completion concept (e.g., those measuring the resistance or impedance associated with the user), the first contact area may comprise any of, but is not limited to: (1) at least a portion of a back of the portable device, (2) at least a portion of a side of the portable device, (3) at least a portion of an antenna of the portable device, (4) at least a portion of a button on the portable device, (5) at least a portion of a button on a detachable device that is attached to the portable device, or (6) at least a portion of a sleeve or case that is on the portable device.

Figure 5A:
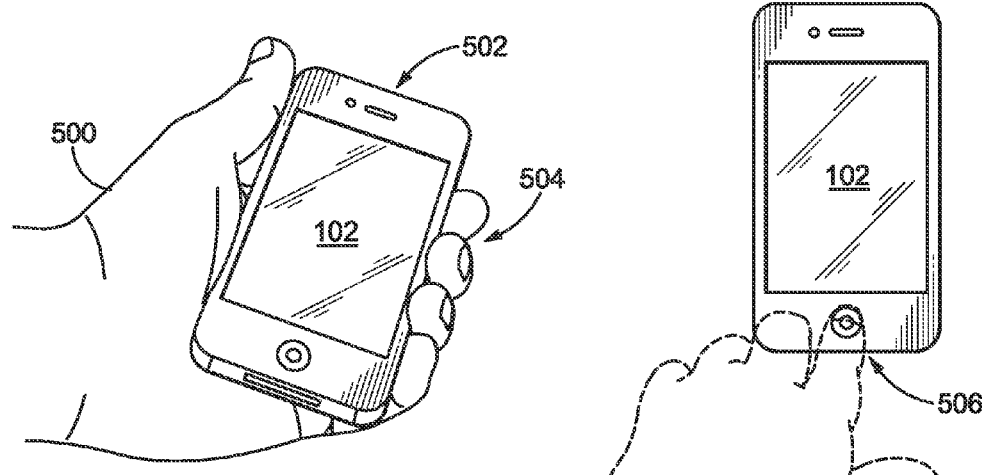
FIGS. 5A-5D illustrate exemplary portions of the user's body that may contact the various embodiments of the first contact area according to some embodiments.

FIGS. 5A-5D illustrate exemplary portions of the user's body that may contact the various embodiments of the first contact area. As understood by a person of skill in the art, any number of other portions of the user's anatomy may alternatively touch the first contact area to provide the first physiological parameter. FIG. 5A shows a user's hand 500 holding or gripping the portable device, as he/she normally would when using the portable device. In this normal or natural holding position, the palm of the hand 500 may contact 502 at least a portion of the back of the portable device according to one embodiment. If the back of the portable device comprises a conductive material, such contact permits capture of the first physiological parameter. In another embodiment, the hand 500 (in particular, the user's finger(s)) may contact 504 at least a portion of the side (e.g., edge) of the portable device. If the side of the portable device comprises a conductive material, such contact permits capture of the first physiological parameter. In still another embodiment, the contact 504 can be between the hand 500 (in particular, the user's finger(s)) and at least a portion of an antenna provided on the side of the portable device. When the antenna comprises a conductive material, such contact provides the first physiological parameter.

Figure 5B:

FIG. 5B shows the user's hand 500 touching 506 at least a portion of a button provided on the portable device (e.g., a location on the portable device outside of the touch sensor panel 102). The button may comprise, but is not limited to, a home button, a menu button, a power button, a volume button, a dedicated sensor for capturing physiological information, and the like. The button comprises a conductive material. The button is not limited to being on a front side of the portable device, and instead may alternatively be located on a side, back, or bottom of the portable device. For example, the volume button may be provided on a side of the portable device.

Figure 5C:
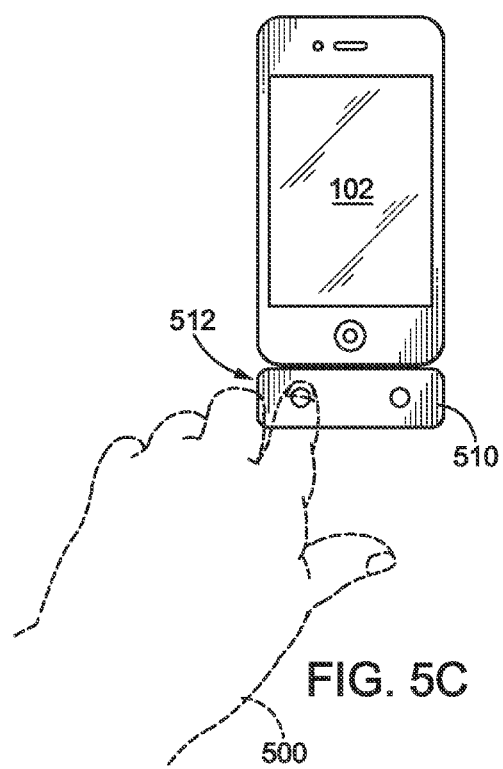

FIG. 5C shows the user's hand 500 touching 512 at least a portion of a button provided on a detachable device 510 attached to the portable device. The detachable device 510 may comprise a dongle or the like, that is configured to establish data (and power) connection with the portable device when attached thereto. The button provided on the detachable device 510 comprises a button or other electrically conductive surface configured to detect an electrical property of the user when the user also touches another portion of the portable device or the detachable device (discussed in detail below).

Figure 5D:
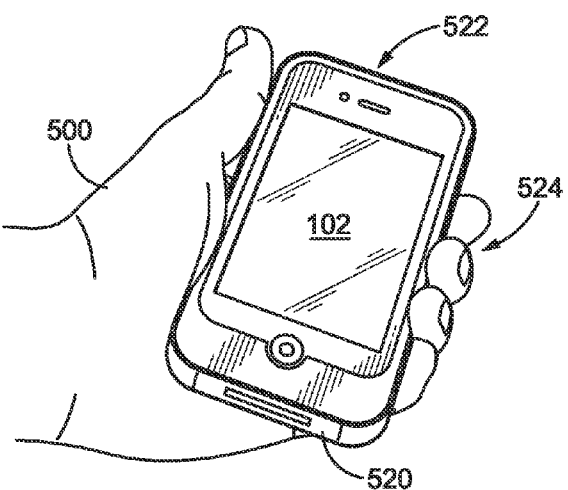

FIG. 5D shows the portable device at least partially encased in a sleeve or case 520. The sleeve/case 520 may encase the back, sides, and the perimeter of the front of the portable device, leaving the touch sensor panel 102 visually and tactilely available for the user. The sleeve/case 520 makes physical contact with at least a portion of a conductive surface of the portable device (e.g., metallic back panel of the portable device). Similar to the holding or gripping position discussed above for FIG. 5A, the user's hand 500 may similarly hold or grip the portable device encased in the sleeve/case 520. The hand 500 then contacts 522 at least portion of the back of the sleeve/case 520 in one embodiment, or the hand 500 (e.g., finger(s)) may contact 524 at least a portion of the side or edge of the sleeve/case 520. The sleeve/case 520 comprises a conductive material.

For physiological measurements based on optical detection of the user's physiological characteristics, the first contact area comprises a light source and a light detector/sensor in proximity to the light source on the portable device (or detachable device as appropriate). As will be apparent to those skilled in the art, the light source and the light detector will often be assemblies having windows or lenses and/or other components that facilitate the device function. These assemblies may integrate the involved components, or the assemblies may be formed when the components are assembled in an operative relationship in the device. The light source and light detector/sensor are positioned relative to each other such that light emitted from the light source enters a portion of the user's body and reflected light exiting the portion of the user's body is detectable by the light detector/sensor. Unlike electrical contact between the user's body and a conductive surface discussed above, physical contact between the light source or light detector/sensor with the user's body is not necessarily required. The first contact area may comprise any of, but is not limited to: (1) a camera and a light emitting diode (LED) flash of the portable device, (2) at least a portion of the touch sensor panel 102 and a pixel sensor included in the touch sensor panel 102, or (3) a light source and light detector/sensor provided in a detachable device attached to the portable device.

Figure 6A:
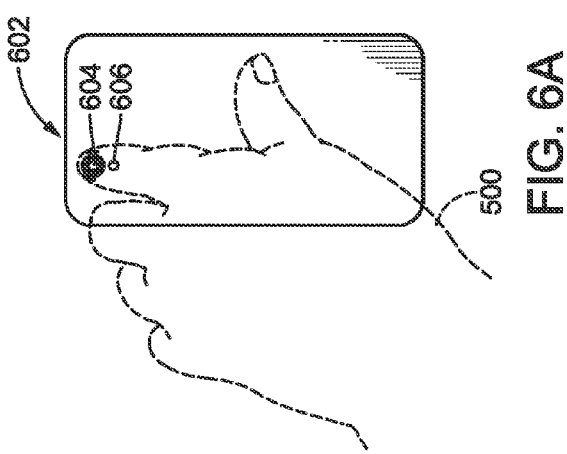
FIGS. 6A-6C illustrate exemplary portions of the user's body that may contact or be in near contact with the various embodiments of the first contact area according to some embodiments.
Figure 6B:
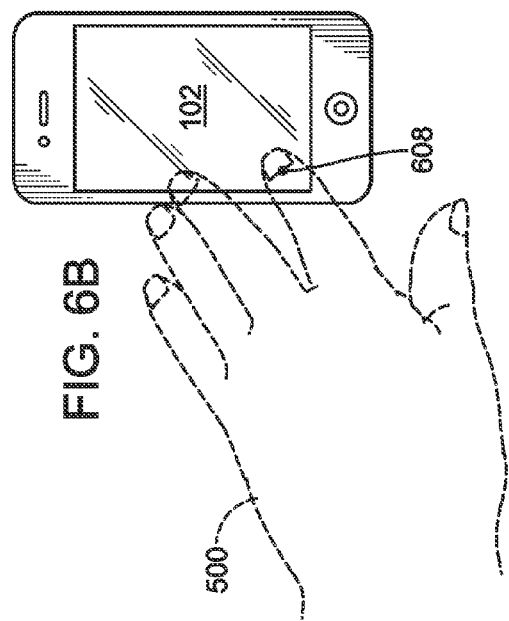
Figure 6C:
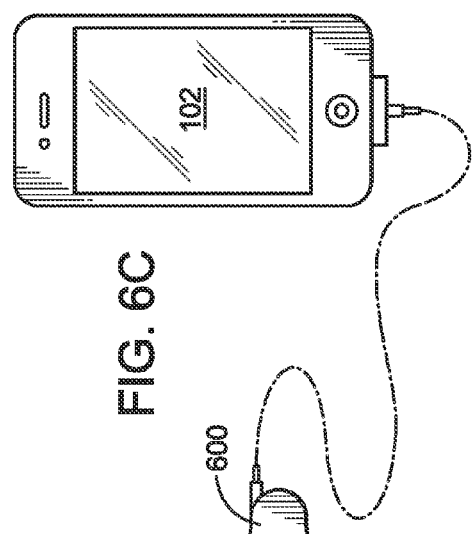

FIGS. 6A-6C illustrate exemplary portions of the user's body that may contact or be in near contact with the various embodiments of the first contact area. As understood by a person of skill in the art, any number of other portions of the user's anatomy may alternatively touch the first contact area to provide the first physiological parameter. FIG. 6A shows the user's hand 500 in contact with or near 602 a camera 604 and a LED 606 provided on the back of the portable device (rear facing camera assembly). The physiological parameter detection module 302 is configured to cause the LED 606 to emit light and the camera 604 to take one or more images (or a video) of the reflected light from the user's hand, and in particular, from the user's finger tip as shown in FIG. 6A. Although not shown, the user's hand 500 may alternatively hold or grip the portable device as shown in FIG. 5A. This natural gripping gesture would also place a user's finger (e.g., pointer finger) over the camera 604 and LED 606 to obtain the first physiological parameter.

FIG. 6B shows the user's hand 500 placed over a portion of the touch sensor panel 102 that includes one (or a set of) pixel sensors 608. In this embodiment, the touch sensor panel 102 includes one or a set of pixel sensors 608 at a pre-determined location in the panel. The pixel sensors 608 may be located at any location in the touch sensor panel 102, such as near or at a corner of the panel. In FIG. 6B, the pixel sensors 608 are shown at the bottom left of the touch sensor panel 102. The physiological parameter detection module 302 is configured to cause the touch sensor panel 102 to illuminate light sufficient to serve as a light source. The pixel sensors 608 are configured to receive the reflected light from the user's hand 500.

FIG. 6C shows a detachable device 600 attached to the portable device, the detachable device 600 comprising a clip-type device including a light source and a light detector/sensor pair. The user's hand 500 (in particular, the tip of a finger) is placed within the opening of the detachable device 600. The detachable device 600 may include a sensor to automatically obtain the first physiological parameter when an object is place within its opening, the device 600 may include a start button or actuator to start detecting the first physiological parameter, or the portable device may control the operation of the detachable device 600.

Next at a block 206, the physiological parameter detection module 302 is configured to obtain a second physiological parameter associated with the user being in contact with a second contact area on the portable device (or detachable device as appropriate). The second contact area (also referred to as a second electrode, second sensor, second contact location, second contact region, etc.) may be located on the portable device or the detachable device that is appropriately attached to the portable device, as discussed in detail below. The material at the second contact area that comes into (electrical) contact with the user comprises a conductive material such as, but not limited to, a metallic or other appropriate material, as discussed earlier herein. The second contact area is distinct from the first contact area. The second contact area may have a different conductive material than the first contact area.

For physiological measurements based on the circuit-completion concept (e.g., those measuring the resistance or impedance associated with the user), the first and second physiological parameters are obtained while the user is simultaneously touching the first and second contact areas. The second contact area may comprise any of, but is not limited to: (1) a particular region or location on the touch sensor panel 102, (2) at least a portion of a button on the portable device, or (3) at least a portion of a button or other sensing location on a detachable device that is attached to the portable device.

FIGS. 7A-7C illustrate exemplary portions of the user's body that may contact the various embodiments of the second contact area. The portion of the user's body that contacts the second contact area is distinct from the portion of the user's body that contacts the first contact area. As understood by a person of skill in the art, any number of other portions of the user's anatomy may alternatively touch the second contact area to provide the second physiological parameter. FIG. 7A shows a user's hand 700 (e.g., a user's finger tip or palm) touching 702 a pre-specified location on the touch sensor panel 102. The pre-specified location is conveyed to the user by displaying a graphical or image item 704 coincident with the pre-specified location on the touch sensor panel 102. The touch sensor panel 102 includes a transparent conductive material layer at least at the pre-specified location. Such conductors are known to those skilled in the art, and may be formed, as just one example, of materials such as indium-tin-oxide (ITO). The conductive layer is provided as the top layer of the touch sensor panel 102, so that the user makes direct electrical contact with the conductive layer. Alternatively, the touch sensor panel 102 may include a conductive layer across the exterior surface of the entire panel (or a desired portion thereof), in which case the user can be instructed to place his/her hand (or other body part) anywhere on the touch sensor panel 102 covered by the conductive layer. In some examples, the surface conductor may be switched in the device to render the conductor electrically neutral except during the measurement operation, so as to avoid any detrimental impact on functioning of the touch screen.

FIG. 7B shows the user's hand 700 touching 706 a button on the portable device (e.g., a sensor that is outside of the touch sensor panel 102). The button comprises, but is not limited to, a home button, a menu button, a power button, a volume button, a dedicated sensor for capturing physiological information, and the like. The button comprises a conductive material. The button is not limited to being on a front side of the portable device, and instead may alternatively be located on a side, back, or bottom of the portable device. For example, the volume button may be provided on a side of the portable device. Also, in various embodiments, these "buttons" may be either mechanical (i.e., having moveable components), or solid state (functioning through electrical or other forms of sensing); and such solid state "buttons" also include virtual buttons depicted on an interactive interface.

FIG. 7C shows the user's hand 700 contacting a sensor located on a detachable device 710. The sensor comprises a conductive material. The detachable device 710 is connected to the portable device via a data (and power) link. The sensor of the detachable device 710 may be controlled by the device itself or the physiological parameter detection module 302 of the portable device.

For physiological measurements based on optical detection, obtaining the second physiological parameter is not required (e.g., block 206 is optional).

Figure 8D:
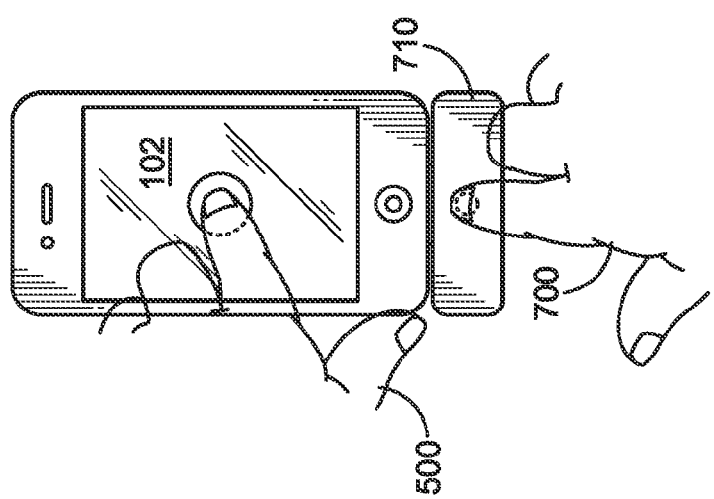
FIGS. 8A-AD provide exemplary illustrations of the user simultaneously touching the portable device and/or the detachable device at two sensor locations according to some embodiments.

FIGS. 8A-8D provide exemplary illustrations of the user simultaneously touching the portable device and/or the detachable device at two sensor locations according to some embodiments. In FIG. 8A, the user is holding the portable device with one hand 500 (e.g., the left hand)—the contact 502 formed between the back of the portable device and the hand 500 or the contact 504 formed between the side or antenna of the portable device and the hand 500—to provide the first physiological parameter. And the user's other hand 700 (e.g., a finger from the right hand) is touching 702 a specified location on the touch sensor panel 102 to provide the second physiological parameter. FIG. 8B shows the user holding the portable device with one hand 500 (e.g., the left hand) while the user's inner wrist of the other hand 700 contacts a specified location on the touch sensor panel 102. In FIG. 8C, the user's hand 500 (e.g., the left hand) is covering a light source, a camera, or both a light source and a camera, while the user's other hand 700 (e.g., finger tip of the right hand) is touching a button (or sensor) located on the detachable device 710 attached to the portable device. In FIG. 8D, the user's hand 500 (e.g., finger tip of the left hand) is touching a specified location on the touch sensor panel 102 while the user's other hand 700 (e.g., finger tip of the right hand) is touching a button (or sensor) located on the detachable device 710 attached to the portable device.

Additional examples of contact configurations between the user and the portable device and/or the detachable device suitable to generate physiological measurements are provided in the table below.

| To obtain first physiological parameter | To obtain second physiological parameter |
|---|---|
| FIG. 5A | FIG. 7A |
| FIG. 5A | FIG. 7B |
| FIG. 5A | FIG. 7C |
| FIG. 5B | FIG. 7A |
| FIG. 5B | FIG. 7B |
| FIG. 5B | FIG. 7C |
| FIG. 5C | FIG. 7A |
| FIG. 5C | FIG. 7B |
| FIG. 5C | FIG. 7C |
| FIG. 5D | FIG. 7A |
| FIG. 5D | FIG. 7B |
| FIG. 5D | FIG. 7C |
| FIG. 6A | — |
| FIG. 6B | — |
| FIG. 6C | — |

In some embodiments, a gyrometer included in the portable device is actuated by the gyrometer module 304 to obtain a gyrometer reading indicative of the orientation of the portable device at the time the user's physiological parameter(s) are obtained (block 208). The gyrometer module 304 checks the gyrometer reading to determine if the portable device is improperly positioned relative to certain reference portion(s) of the user's body (block 210). For certain kinds of blood dynamic measurements (e.g., pulse measurements), how the user holds the portable device overall relative to his/her heart affects the accuracy of the resulting physiological measurement. If, for example, the portable device (and the detachable device attached to the portable device) is too high or too low relative to the user's heart, the resulting pulse measurement may be inaccurate. In another example, an accelerometer included in the portable device may be used to determine whether the user is motionless during the physiological measurement; and if motion parameter is identified (for example, direction, speed, force) that meets a threshold criteria indicating that it could reflect a basis for error in the measurement, appropriate feedback can be provided. This feedback could include, for example, restarting the measurement process or some portion thereof; or providing a cautionary warning to the user, such as through a displayed image or displayed text, and/or an audible signal. In still another example, a front-facing camera included in the portable device may be used to determine the position and orientation of the portable device with respect to the user during measurement. Again, if the position or orientation is determined to be less than desirable (as may be determined by comparing the image properties (such as for example, the angle of facial recognition) to one or more references), then appropriate feedback, as described above, may be provided to the user.

Figure 9:
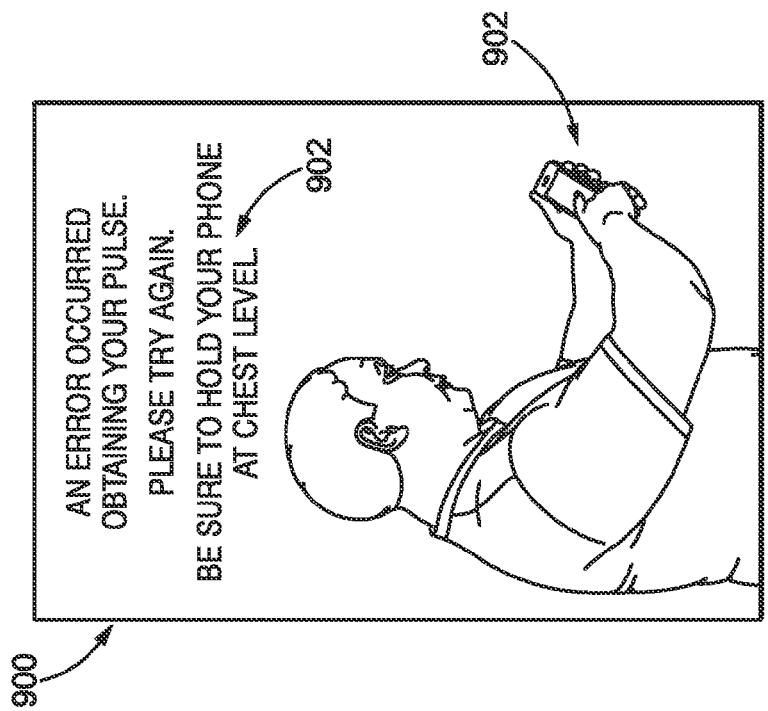
FIG. 9 illustrates an exemplary user interface presented to the user on the touch sensor panel providing guidance to achieve proper position/orientation during measurement according to some embodiments.

If the gyrometer module 304 determines that there is improper position/orientation (yes branch 212), then the information display module 300 causes the touch sensor panel 102 to display instructions to the user to correct the position/orientation (block 214). As an example, FIG. 9 illustrates an exemplary user interface 900 presented to the user on the touch sensor panel 102 providing guidance (e.g., text and image items 902) for the user to achieve proper position/orientation during measurement. Once one or more user interface pages are displayed to the user pertaining to achieving proper position/orientation, instructions regarding where the user should touch the portable device (and portable device as appropriate) are re-displayed to the user (returns to block 202).

For physiological measurements (e.g., body water content or body fat content measurements) where the position or orientation of the portable device (and detachable device as appropriate) relative to the user's body is not relevant, blocks 208, 210, 214 may be omitted.

If at block 210 the position/orientation is deemed to be proper (no branch 216), then the obtained physiological parameter(s) are processed by hardware, firmware, and/or software to generate a physiological measurement corresponding to the captured physiological parameter(s) (block 218). Different processing treatment may be required depending on the particular physiological measurement desired and/or the type of physiological parameter(s) obtained in blocks 204, 206. A physiological measurement calculation module 306 is configured to perform the conversion calculations. For example, the first physiological parameter comprising optical data may be filtered and amplified by circuitry prior to undergoing software-based processing such as Fourier frequency analysis. As another example, physiological parameters that are resistive measurements from one side of the user's upper torso to the other side comprise Lead 1 ECG signals. Such Lead 1 ECG signals can be translated or converted into a heart rate measurement using known algorithmic methods. An exemplary algorithmic method includes digital preprocessing to reject wideband noise and baseline drift, followed by multiscale analysis of the preprocessed signal for QRS complexes, and spectral analysis for characteristic frequency content (e.g., sinus rhythms or ventricular fibrillation (VFIB)). Alternatively, the detected Lead 1 ECG signals may undergo no or minimal processing and thus remain as ECG measurements. Calculation of body water content or body fat content from the first and second physiological parameters may also be performed using known algorithmic methods by the physiological measurement calculation module 306. Examples of suitable algorithmic methods for body fat content determination are known in the art, as demonstrated, for example, by Ursula G. Kyle et al., "Bioelectrical impedance analysis part I: review of principles and methods," *Clinical Nutrition*, Vol. 23 (5): 1226-1243 (2004). Examples of suitable algorithmic methods for body water content determination are known in the art, as demonstrated, for example by G. Bedogni et. al., *European Journal of Clinical Nutrition*, Vol. 56, Number 11, pp. 1143-1148 (currently available at http://www.nature.com/ejcn/journal/v56/n11/full/1601466a.html).

Next at a block 220, the calculated physiological measurement is displayed on the touch sensor panel 102. The information display module 300 facilitates display of the physiological measurement in the user interface provided to the user in block 202. For example, the user's pulse rate, body fat content, and/or body water content can be displayed as measurement items 410 (FIG. 4A).

The calculated physiological measurement along with related information (e.g., time and date stamp, user identifier) can be saved (block 222) by a post-calculation module 308. The post-calculation module 308 may also facilitate transmission of the physiological measurement (and related information) over a network, such as over a cellular network or WiFi, to a remote device. By saving and/or communicating one or more physiological measurements over time, such information may illuminate trends for useful health assessment.

It is understood that one or more blocks of FIG. 2 may be performed in a different sequence than shown in FIG. 2. For example, block 208 may be performed before blocks 204 or 206. One or more blocks of FIG. 2 may also be performed simultaneously instead of serially as shown in flow diagram 200. Blocks 204, 206, 208, for example, may be performed in parallel with each other, or blocks 220 and 222 may be performed at the same time.

In this manner, portable devices, such as smart phones and tablets, are used to generate one or more physiological measurements associated with a user. In some embodiments, the user interacts with the portable device as he/she normally would, and the portable device is configured to sense physiological parameters about the user and translate it into useful health assessment information. Such information—physiological measurements—includes ECG measurements, pulse measurements, body fat content measurement, and/or body water content measurement. In other embodiments, the portable device provides instructions for the user to position body part(s) relative to the portable device to obtain the physiological parameters.

Part of the appeal of portable devices is their versatility in performing a variety of tasks that spans a person's personal and work needs. Such portable devices include sophisticated processors and inputs/outputs that are adaptable over time to changing needs. This means one device can take the place of multiple devices, each multiple device only capable of a specific function. Another appeal of portable devices is their portability. Because they are small enough for a person to put in a pocket or otherwise carry around, they are more likely to be used rather than dedicated devices. Moreover, because of the popularity of portable devices, these devices enjoy a high amount of design resources, which tends to result in a more refined user interface than dedicated physiological measurements devices serving a smaller customer base.

Additionally, because many of the example portable devices (like phones, tablets, laptops, etc.) have Wifi and/or cellular communication capability, the physiological measurements can be communicated, either automatically or pursuant to a user input, to a database or other record keeping facility, or to an intended recipient (such as a health care professional. Alternatively, the measurements can be downloaded, such as though a syncing function, with another electronic device.

Figure 10:
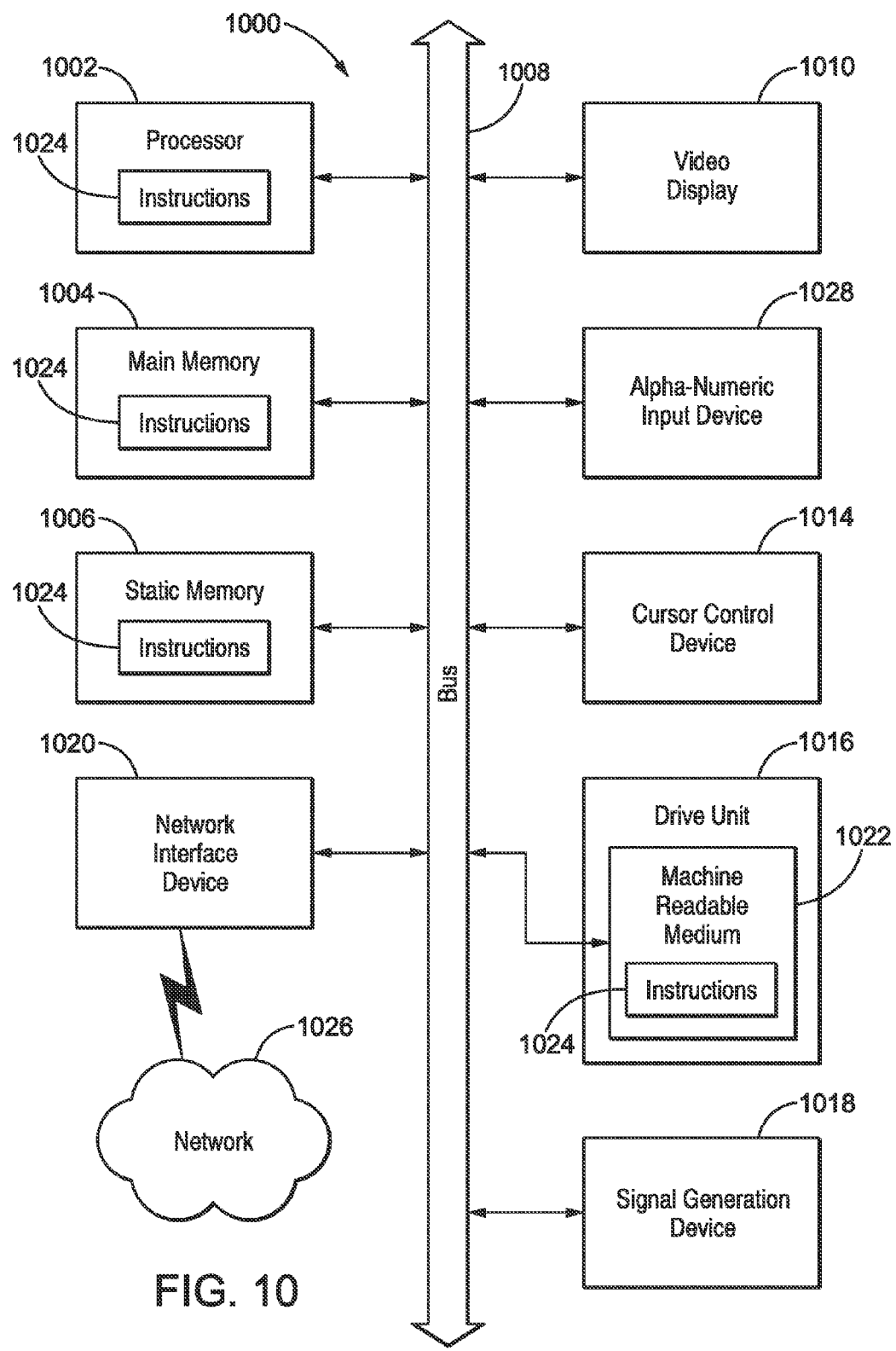
FIG. 10 depicts a block diagram representation of an example architecture for the controller assembly.

FIG. 10 depicts a block diagram representation of an example architecture for the controller assembly 104. Although not required, in many configurations for the controller assembly 104 would include one or more microprocessors which will operate pursuant to one or more sets of instructions for causing the machine to perform any one or more of the methodologies discussed herein.

The example controller assembly 1000 includes a processor 1002 (e.g., a central processing unit (CPU), a graphics processing unit (GPU) or both), a main memory 1004 and a static memory 1006, which communicate with each other via a bus 1008. The controller assembly 1000 may further include a video display unit 1010 (e.g., a liquid crystal display (LCD) or a cathode ray tube (CRT)). The controller assembly 1000 may also include an alphanumeric input device 1012 (e.g., a keyboard, mechanical or virtual), a cursor control device 1014 (e.g., a mouse or track pad), a disk drive unit 1016, a signal generation device 1018 (e.g., a speaker), and a network interface device 1020.

The disk drive unit 1016 includes a machine-readable medium 1022 on which is stored one or more sets of executable instructions (e.g., apps) embodying any one or more of the methodologies or functions described herein. In place of the disk drive unit, a solid-state storage device, such as those comprising flash memory may be utilized. The executable instructions may also reside, completely or at least partially, within the main memory 1004 and/or within the processor 1002 during execution thereof by the controller assembly 1000, the main memory 1004 and the processor 1002 also constituting machine-readable media. Alternatively, the instructions may be only temporarily stored on a machine-readable medium within controller 1000, and until such time may be received over a network 1026 via the network interface device 1020.

While the machine-readable medium 1022 is shown in an example embodiment to be a single medium, the term "machine-readable medium" as used herein should be taken to include a single medium or multiple media (e.g., a centralized or distributed database, and/or associated caches and servers) that store the one or more sets of instructions. The term "machine-readable medium" or "computer-readable medium" shall be taken to include any tangible non-transitory medium (which is intended to include all forms of memory, volatile and non-volatile) which is capable of storing or encoding a sequence of instructions for execution by the machine.

Many additional modifications and variations may be made in the techniques and structures described and illustrated herein without departing from the spirit and the scope of the present invention. For example, the described methods and systems have been described for passive measurement of electrical or optical properties of the user's physiology. However, active-type of measurements may also be possible. As an example, the user may contact two electrodes on a detachable device and the detachable device may further send a small electric current through the user's body. The resistance measured between the two electrodes with the introduced electric current provides a measure of body fat. Accordingly, the present invention should be clearly understood to be limited only by the scope of the claims and equivalents thereof.

What is claimed is:

1. A system for obtaining a physiological measurement, comprising:
   a touch-sensitive display included in a first portable device;
   a first contact area located at a first location in the system;
   a second contact area located at a second location in the system, the first contact area electrically isolated from the second contact area;
   a gyrometer included in the first portable device, wherein the gyrometer is configured to detect orientation of the first portable device and to generate a signal indicative of an improper orientation of the first portable device for receiving a selected signal; and
   a processor in communication with each of the touch-sensitive display, the first contact area, the second contact area, and the gyrometer, the processor configured to receive the selected signal when a user simultaneously contacts the first and second contact areas, wherein the selected signal is associated with a first physiological parameter, and is further configured to process the received selected signal to determine the first physiological parameter.

2. The system of claim 1, wherein at least the first contact area, the touch-sensitive display, and the processor are included in the first portable device.

3. The system of claim 1, wherein the first portable device comprises a smart phone.

4. The system of claim 2, wherein the first location of the first contact area comprises a conductive portion of the first portable device.

5. The system of claim 4, wherein the conductive portion comprises at least one of an antenna, a physical button, a sensor, and a casing of the first portable device.

6. The system of claim 1, wherein at least one of the first and second contact areas is included in a second portable device configured to be electrically coupled to and detached from the first portable device.

7. The system of claim 1, wherein the touch-sensitive display displays information for the user to correct orientation of the first portable device.

8. The system of claim 1, wherein the second contact area comprises a top conductive layer of the touch-sensitive display.

9. The system of claim 1, wherein the second location comprises a pre-determined location on the touch-sensitive display.

10. The system of claim 9, wherein an image is displayed on the touch-sensitive display corresponding to the pre-determined location.

11. The system of claim 8, wherein a finger or an inner wrist of the user contacts the second contact area.

12. The system of claim 1, further comprising a camera and a light emitting diode (LED), wherein at least one of the camera and the LED comprise the first contact area.

13. The system of claim 1, wherein the touch-sensitive display comprises a liquid crystal display (LCD) and a pixel sensor, wherein the pixel sensor is included in the first contact area.

14. The system of claim 1, wherein at least the second contact area is included in a second portable device, wherein the second portable device is configured to be electrically coupled to and detachable from the first portable device.

15. The system of claim 14, wherein the second portable device comprises a cover for the first portable device or a dongle.

16. The system of claim 1, wherein the touch-sensitive display is configured to display instructions for the user to provide the selected signal.

17. The system of claim 1, wherein the selected signal comprise parameters from opposite sides of the user's torso.

18. The system of claim 1, wherein the first physiological parameter comprises an electrocardiogram (ECG) measurement, a pulse measurement, or a bioelectrical impedance analysis (BIA) measurement.

19. The system of claim 1, further comprising a transmitter in communication with the processor, the transmitter configured to transmit the first physiological parameter to a remote device.

20. A method for obtaining a physiological measurement, the method comprising:
   determining, using a pyrometer, that a portable device is improperly oriented relative to a portion of a user's body;
   displaying, on a touch-sensitive display of the portable device, information comprising instructions for the user to correct orientation of the portable device;
   displaying information on the touch-sensitive display, the displayed information including identification of a first location on the portable device to be touched by the user;
   receiving, in response to the user touching the first location, a first physiological parameter at the first location, the first physiological parameter associated with a physiological property of the user; and
   generating the physiological measurement using the first physiological parameter.

21. The method of claim 20, wherein the first location comprises at least a portion of the touch-sensitive display.

22. The method of claim 20, further comprising:
receiving, in response to the user touching a second location, a second physiological parameter at the second location, the first location is distinct from the second location and the user simultaneously touches the first location and the second location,
wherein the generating of the physiological measurement is based on the first physiological parameter and the second physiological parameter.

23. The method of claim 22, wherein the second location is included on a detachable device in electrical contact with the portable device.

24. The method of claim 20, further comprising transmitting the physiological measurement to a remote device.

* * * * *

UNITED STATES PATENT AND TRADEMARK OFFICE
CERTIFICATE OF CORRECTION

PATENT NO. : 8,988,372 B2  
APPLICATION NO. : 13/402452  
DATED : March 24, 2015  
INVENTOR(S) : Messerschmidt et al.

Page 1 of 1

It is certified that error appears in the above-identified patent and that said Letters Patent is hereby corrected as shown below:

On the Title Page

On page 2, in column 1, References Cited, under "Other Publications", line 1, delete "part 1" and insert --part I--, therefor In the Claims In column 14, line 51, in Claim 20, delete "pyrometer," and insert --gyrometer,--, therefor Signed and Sealed this  
Twenty-fifth Day of August, 2015

Michelle K. Lee  
*Director of the United States Patent and Trademark Office*